US007309360B2

(12) United States Patent
Tornier et al.

(10) Patent No.: US 7,309,360 B2
(45) Date of Patent: Dec. 18, 2007

(54) SET OF HUMERAL COMPONENTS FOR TOTAL SHOULDER PROSTHESIS

(75) Inventors: Alain Tornier, Saint Ismier (FR); Francois Sirveaux, Villers les Nancy (FR); Gilles Walch, Lyons (FR); Daniel Mole, Nancy (FR); Christophe Levigne, Caluire (FR); Pascal Boileau, Nice (FR); Luc Favard, Moutlouis (FR)

(73) Assignee: Tornier, Saint Ismier (FR)

( * ) Notice: Subject to any disclaimer, the term of this patent is extended or adjusted under 35 U.S.C. 154(b) by 0 days.

(21) Appl. No.: 11/148,377

(22) Filed: Jun. 9, 2005

(65) Prior Publication Data
US 2005/0278031 A1 Dec. 15, 2005

Related U.S. Application Data

(60) Provisional application No. 60/579,259, filed on Jun. 15, 2004.

(30) Foreign Application Priority Data
Jun. 15, 2004 (FR) .................................. 04 06470

(51) Int. Cl.
*A61F 2/40* (2006.01)
(52) U.S. Cl. .............................. 623/19.12; 623/19.13; 623/19.14
(58) Field of Classification Search ............ 623/19.11, 623/19.12, 19.13, 19.14
See application file for complete search history.

(56) References Cited

U.S. PATENT DOCUMENTS

| 3,694,820 A | 10/1972 | Scales et al. |
| 3,815,157 A | 6/1974 | Skorecki et al. |
| 3,842,442 A | 10/1974 | Kolbel |
| 3,869,730 A | 3/1975 | Skobel |
| 3,916,451 A | 11/1975 | Buechel et al. |
| 3,978,528 A | 9/1976 | Crep |
| 3,979,778 A | 9/1976 | Stroot |
| 4,003,095 A | 1/1977 | Gristina |
| 4,030,143 A | 6/1977 | Elloy et al. |
| 4,040,131 A | 8/1977 | Gristina |

(Continued)

FOREIGN PATENT DOCUMENTS

CH            507704           5/1971

(Continued)

OTHER PUBLICATIONS

John M. Fenlin Jr., M.D. Symposium on Surgery of the Shoulder, "Total Glenohumeral Joint Replacement," *Othopedic Clinics of North America*, vol. 6, No. 2, Apr. 1975, pp. 565-583.

*Primary Examiner*—Thomas J Sweet
(74) *Attorney, Agent, or Firm*—Faegre & Benson LLP

(57) ABSTRACT

A set of humeral components for a total shoulder prosthesis, wherein each component is formed by an anchoring stem and a metaphyseal part which defines a concave surface of articulation in the form of a portion of a sphere. The offset between an axis of symmetry of this surface and a central axis of the metaphyseal part varies between the different components of the set. This makes it possible to limit or to avoid, by a reasoned choice of the humeral component used, an interference with the pillar of the scapula during a movement of adduction.

55 Claims, 2 Drawing Sheets

U.S. PATENT DOCUMENTS

| | | | |
|---|---|---|---|
| 4,135,517 A | 1/1979 | Reale | |
| 4,179,758 A | 12/1979 | Gristina | |
| 4,206,517 A | 6/1980 | Pappas et al. | |
| 4,693,723 A | 9/1987 | Gabard | |
| 4,822,370 A | 4/1989 | Schelhas | |
| 4,865,605 A | 9/1989 | Dines et al. | |
| 4,865,609 A | 9/1989 | Roche | |
| 4,919,670 A | 4/1990 | Dale et al. | |
| 4,957,510 A | 9/1990 | Cremascoli | |
| 4,963,155 A | 10/1990 | Lazzeri et al. | |
| 5,080,673 A | 1/1992 | Burkhead et al. | |
| 5,080,685 A | 1/1992 | Bolesky et al. | |
| 5,135,529 A | 8/1992 | Paxson et al. | |
| 5,163,961 A | 11/1992 | Harwin | |
| 5,171,289 A | 12/1992 | Tornier | |
| 5,181,928 A | 1/1993 | Bolesky et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A * | 5/1994 | Rockwood et al. | 623/19.14 |
| 5,314,485 A | 5/1994 | Judet | |
| 5,326,359 A | 7/1994 | Oudard | |
| 5,358,526 A | 10/1994 | Tornier | |
| 5,405,399 A | 4/1995 | Tornier | |
| 5,425,779 A | 6/1995 | Schlosser | |
| 5,429,639 A | 7/1995 | Judet | |
| 5,458,650 A | 10/1995 | Carret et al. | |
| 5,462,563 A | 10/1995 | Shearer et al. | |
| 5,505,731 A | 4/1996 | Tornier | |
| 5,507,817 A | 4/1996 | Craig et al. | |
| 5,507,818 A | 4/1996 | McLaughlin | |
| 5,507,824 A | 4/1996 | Lennox | |
| 5,549,682 A | 8/1996 | Roy | |
| 5,580,352 A | 12/1996 | Sekel | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,766,256 A | 6/1998 | Oudard et al. | |
| 5,824,106 A | 10/1998 | Fournol | |
| 5,879,395 A | 3/1999 | Tornier et al. | |
| 5,902,340 A | 5/1999 | White et al. | |
| 5,910,171 A | 6/1999 | Kummer et al. | |
| 5,961,555 A | 10/1999 | Huebner | |
| 5,984,927 A | 11/1999 | Wenstrom, Jr. et al. | |
| 6,033,439 A | 3/2000 | Camino et al. | |
| 6,045,582 A | 4/2000 | Prybyla | |
| 6,102,953 A | 8/2000 | Huebner | |
| 6,129,764 A | 10/2000 | Servidio | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,197,062 B1 | 3/2001 | Fenlin | |
| 6,197,063 B1 | 3/2001 | Dews | |
| 6,206,925 B1 | 3/2001 | Tornier | |
| 6,228,120 B1 | 5/2001 | Leonard et al. | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,379,387 B1 | 4/2002 | Tornier | |
| 6,436,147 B1 | 8/2002 | Zweymuller | |
| 6,454,809 B1 | 9/2002 | Tornier | |
| 6,475,243 B1 | 11/2002 | Sheldon et al. | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,620,197 B2 | 9/2003 | Maroney et al. | |
| 6,626,946 B1 | 9/2003 | Walch et al. | |
| 6,736,851 B2 | 5/2004 | Maroney et al. | |
| 6,761,740 B2 | 7/2004 | Tornier | |
| 6,767,368 B2 | 7/2004 | Tornier | |
| 6,790,234 B1 * | 9/2004 | Frankle | 623/19.12 |
| 6,802,864 B2 | 10/2004 | Tornier | |
| 6,824,567 B2 | 11/2004 | Tornier et al. | |
| 6,890,357 B2 | 5/2005 | Tornier | |
| 6,953,478 B2 | 10/2005 | Bouttens et al. | |
| 6,969,406 B2 | 11/2005 | Tornier | |
| 7,011,686 B2 | 3/2006 | Ball et al. | |
| 7,033,396 B2 | 4/2006 | Tornier | |
| 2001/0049561 A1 | 12/2001 | Dews et al. | |
| 2002/0138148 A1 | 9/2002 | Hyde, Jr. | |
| 2003/0009170 A1 | 1/2003 | Tornier | |
| 2003/0009171 A1 | 1/2003 | Tornier | |
| 2003/0028198 A1 | 2/2003 | Tornier et al. | |
| 2003/0097183 A1 | 5/2003 | Rauscher et al. | |
| 2003/0114933 A1 | 6/2003 | Bouttens et al. | |
| 2003/0149485 A1 | 8/2003 | Tornier | |
| 2003/0158605 A1 | 8/2003 | Tornier | |
| 2004/0064189 A1 | 4/2004 | Maroney et al. | |
| 2004/0064190 A1 * | 4/2004 | Ball et al. | 623/19.14 |
| 2004/0134821 A1 | 7/2004 | Tornier | |
| 2004/0210220 A1 | 10/2004 | Tornier | |
| 2004/0215200 A1 | 10/2004 | Tornier et al. | |
| 2004/0220673 A1 | 11/2004 | Pria | |
| 2004/0220674 A1 | 11/2004 | Pria | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0203536 A1 | 9/2005 | Laffargue et al. | |
| 2005/0278030 A1 * | 12/2005 | Tornier et al. | 623/19.11 |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2006/0015185 A1 | 1/2006 | Chambat et al. | |
| 2006/0020344 A1 | 1/2006 | Schultz et al. | |
| 2006/0173457 A1 | 8/2006 | Tornier | |
| 2006/0235538 A1 | 10/2006 | Rochetin et al. | |

FOREIGN PATENT DOCUMENTS

| | | | |
|---|---|---|---|
| DE | 19509037 | | 9/1996 |
| DE | 19630298 | | 1/1998 |
| EP | 0257359 | | 3/1988 |
| EP | 0299889 | | 1/1989 |
| EP | 549480 | | 6/1993 |
| EP | 0599429 | | 6/1994 |
| EP | 617934 | | 10/1994 |
| EP | 0664108 | | 7/1995 |
| EP | 0679375 | | 11/1995 |
| EP | 0712617 | | 5/1996 |
| EP | 715836 | | 6/1996 |
| EP | 0797694 | | 10/1997 |
| EP | 0903127 | | 3/1999 |
| EP | 903128 | | 3/1999 |
| EP | 927548 | | 7/1999 |
| EP | 1062923 | | 12/2000 |
| EP | 1064890 | | 1/2001 |
| EP | 1195149 | | 4/2002 |
| EP | 1402854 | | 3/2004 |
| EP | 1402854 | A2 * | 3/2004 |
| FR | 2545352 | | 11/1984 |

| | | | | | | |
|---|---|---|---|---|---|---|
| FR | 2574283 | 6/1986 | | WO | WO 98/46172 | 10/1996 |
| FR | 2652498 | 4/1991 | | WO | WO 99/49792 | 10/1999 |
| FR | 2664809 | 1/1992 | | WO | WO 99/65413 | 12/1999 |
| FR | 2699400 | 6/1994 | | WO | WO 00/15154 | 3/2000 |
| FR | 2721200 | 12/1995 | | WO | WO 00/41653 | 7/2000 |
| FR | 2726994 | 5/1996 | | WO | WO 01/47442 | 7/2001 |
| FR | 2737107 | 1/1997 | | WO | WO 02/39931 | 5/2002 |
| FR | 2835425 | 8/2003 | | WO | WO 02/39933 | 5/2002 |
| FR | 2836039 | 8/2003 | | WO | WO 02/067821 | 9/2002 |
| WO | WO 91/07932 | 6/1991 | | WO | 03/005933 | 1/2003 |
| WO | 93/09733 | 5/1993 | | WO | WO 03/005933 | 1/2003 |
| WO | WO 93/09733 | 5/1993 | | | | |
| WO | WO 96/17553 | 6/1996 | | * cited by examiner | | |

SET OF HUMERAL COMPONENTS FOR TOTAL SHOULDER PROSTHESIS

CROSS REFERENCE TO RELATED APPLICATIONS

This application claims the benefit of U.S. provisional application for patent Ser. No. 60/579,259, filed Jun. 15, 2004, and also claims priority of French application for patent 04 06470, filed Jun. 15, 2004.

BACKGROUND OF THE INVENTION.

The present invention relates to a set of humeral components for a total shoulder prosthesis, as well as to a prosthesis and to a method for installing such a prosthesis.

DESCRIPTION OF THE RELATED ART

In the domain of total shoulder prostheses, it is known, for example from U.S. Pat. No. 3 978 528, from EP-A-0 299 899 or from FR-A-2 836 039, to form a prosthesis in which a convex articular surface is secured to a glenoid cavity, while a concave articular surface is secured to a humerus, the cooperation of these surfaces making it possible to recreate a joint of the shoulder. With these known prostheses, it may happen, during a movement of adduction, that a portion of a metaphyseal part of the humeral component engages the pillar of the scapula, which limits this movement and may prove painful, and even cause damage to the prosthesis.

It is a more particular object of the present invention to overcome these drawbacks by proposing a set of humeral components which allows the surgeon to optimize the relative positioning of the prosthetic components, as a function of the patient's anatomy.

SUMMARY OF THE INVENTION

In that spirit, the invention relates to a set of humeral components for a total shoulder prosthesis, in which each component is formed by an anchoring stem and a metaphyseal part which defines a concave surface of articulation globally in the form of a portion of sphere. This set of components is characterized in that the offset between the central axis of the metaphyseal part and the axis of symmetry of the concave surface of articulation of the different components is variable.

Thanks to the invention, the concave articular surface of the different humeral components may be so positioned, with respect to the outer surface of the metaphyseal part, that the interferences of the metaphyseal part with the pillar of the scapula are minimized, and even eliminated.

According to advantageous but non-obligatory aspects, a set of humeral components may incorporate one or more of the following characteristics, taken in any technically possible combinations:

the axis of symmetry of the articular surface and the central axis of the metaphyseal part of each component are substantially parallel;

the axis of symmetry of the articular surface of at least one component is disposed, with respect to the central axis of the metaphyseal part, opposite a median axis of the anchoring stem such that the surface of articulation of the at least one component advantageously extends to the immediate vicinity of the edge of the metaphyseal part, or is even intersected by this edge, opposite that part of the edge located generally in line with the anchoring stem;

the different components have substantially the same shape, except for the position of the articular surface in the metaphyseal part;

the angle of inclination of the axis of symmetry of the articular surface with respect to the median axis of the stem has substantially the same value for all the components; and the afore-mentioned offset may be zero for one of the humeral components, the axes in that case being merged.

The invention also relates to a total shoulder prosthesis which comprises a humeral component selected from a set of components as described hereinabove. Such a prosthesis is more easily adaptable to the patient's morphology.

According to an advantageous aspect of the invention, such a prosthesis comprises, in addition, a glenoid component which forms a convex surface of articulation centered on an axis of symmetry which is not perpendicular to a rear face of this component intended to come into abutment against the glenoid cavity. This aspect of the invention makes it possible to "compensate" for a defect in parallelism between a resectioned surface of the glenoid cavity against which the glenoid component abuts and an axis of the patient's spinal column.

Finally, the invention relates to a method for surgically implanting a total shoulder prosthesis which comprises steps consisting in:

preparing the bones to permit positioning of a glenoid component and a humeral component;

securing on the glenoid cavity a the glenoid component defining a convex articular surface;

selecting, from a set of humeral components, a humeral component provided with a concave articular surface adapted to cooperate with a convex articular surface of the glenoid component, this component substantially not interfering or interfering only little with the pillar of the scapula during a movement of adduction, and securing the humeral component on the humerus.

The method of the invention may be carried out by a surgeon installing a total shoulder prosthesis, the selection of the most adapted humeral component being able to be effected during the surgical operation, or in advance during the pre-op check-up.

BRIEF DESCRIPTION OF THE DRAWINGS

The invention will be more readily understood and other advantages thereof will appear more clearly in the light of the following description of a set of humeral components in accordance with its principle and of the installation of a total shoulder prosthesis by means of this set of components, given solely by way of example and made with reference to the accompanying drawings, in which.

DESCRIPTION OF PREFERRED EMBODIMENT

Figure 1:
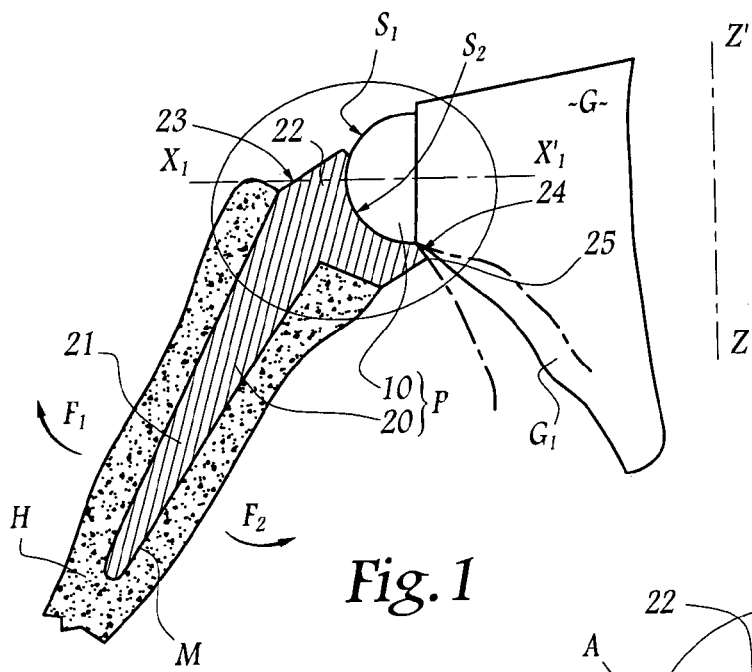
FIG. 1 schematically shows a total shoulder prosthesis installed on a patient and comprising a humeral component shown in section, issuing from a set of components according to the invention.

Referring now to the drawings, the prosthesis P shown in FIG. 1 comprises a glenoid component 10 which is fixed to the glenoid cavity G by any appropriate means, for example in accordance with the technical teaching of FR-A-2 836 039, and which defines a convex articular surface $S_1$ substantially in the form of a demi-sphere.

The prosthesis P also comprises a humeral component 20 formed by an anchoring stem 21 and a metaphyseal part 22. The stem 21 is globally rectilinear and adapted to be introduced in the medullary canal M of the humerus H, while the metaphyseal part 22 projects beyond this canal and defines a concave articular surface $S_2$ in the form of a portion of sphere.

Figure 1A:
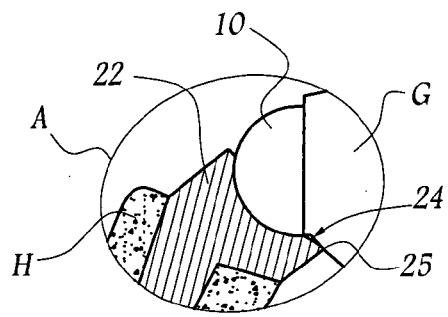
FIG. 1A is a view of detail A in FIG. 1 in configuration of interference between the humeral component and the pillar of the scapula.
Figure 2:
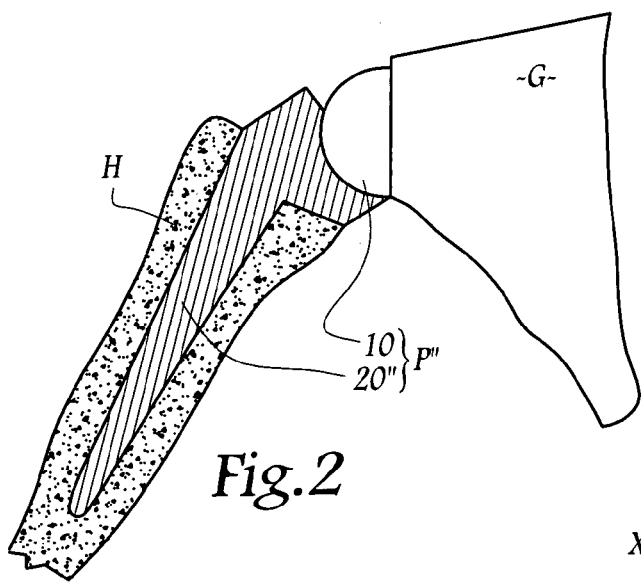
FIG. 2 is a view similar to FIG. 1, whereas the humeral component is different from the one used in the prosthesis of FIG. 1.

In FIGS. 1, 1A and 2, the glenoid cavity 4 and the component 10 are shown in side view, while the humerus H and component 20 are shown in longitudinal section.

The surfaces $S_1$ and $S_2$ are adapted to constitute a sliding articulation and have substantially equal radii.

The external shape of the metaphyseal part 22 is globally cylindrical with circular base and 23 denotes its outer radial surface. Furthermore, 24 denotes its end surface which is globally planar and in which the concave surface $S_2$ is hollowed. Finally, 25 denotes the outer peripheral edge which connects the surfaces 23 and 24 and which is circular like surface 23.

Central axis $X_{22}$ of the metaphyseal part 22 is defined by an axis perpendicular to the surface 24 and passing through an imaginary center of this surface. In practice, axis $X_{22}$ is an axis of symmetry of the edge 25.

In certain configurations, the surface 24 may be eliminated. In that case, the edge 25 directly joins the surfaces $S_2$ and 23, and the axis $X_{22}$ is defined as the axis of symmetry of the edge 25.

The humerus H is assumed to undergo movements of abduction represented by arrow $F_1$ and movements of adduction represented by arrow $F_2$ in FIG. 1.

At the end of adduction stroke, those parts of the surface 24 and of the edge 25 most remote from the stem 21 are capable of hitting the pillar of the scapula $G_1$, i.e. that part of the glenoid cavity G located in the vicinity of the component 10 below the latter when the patient is standing up. In this configuration of interference shown in FIG. 1A, the patient feels discomfort, which is detrimental to the success of the operation.

It will be understood that this configuration of interference is not systematic insofar as the pillar of the scapula $G_1$ may take different shapes, as shown, in broken lines only, in FIG. 1.

Figures 3, 3A:
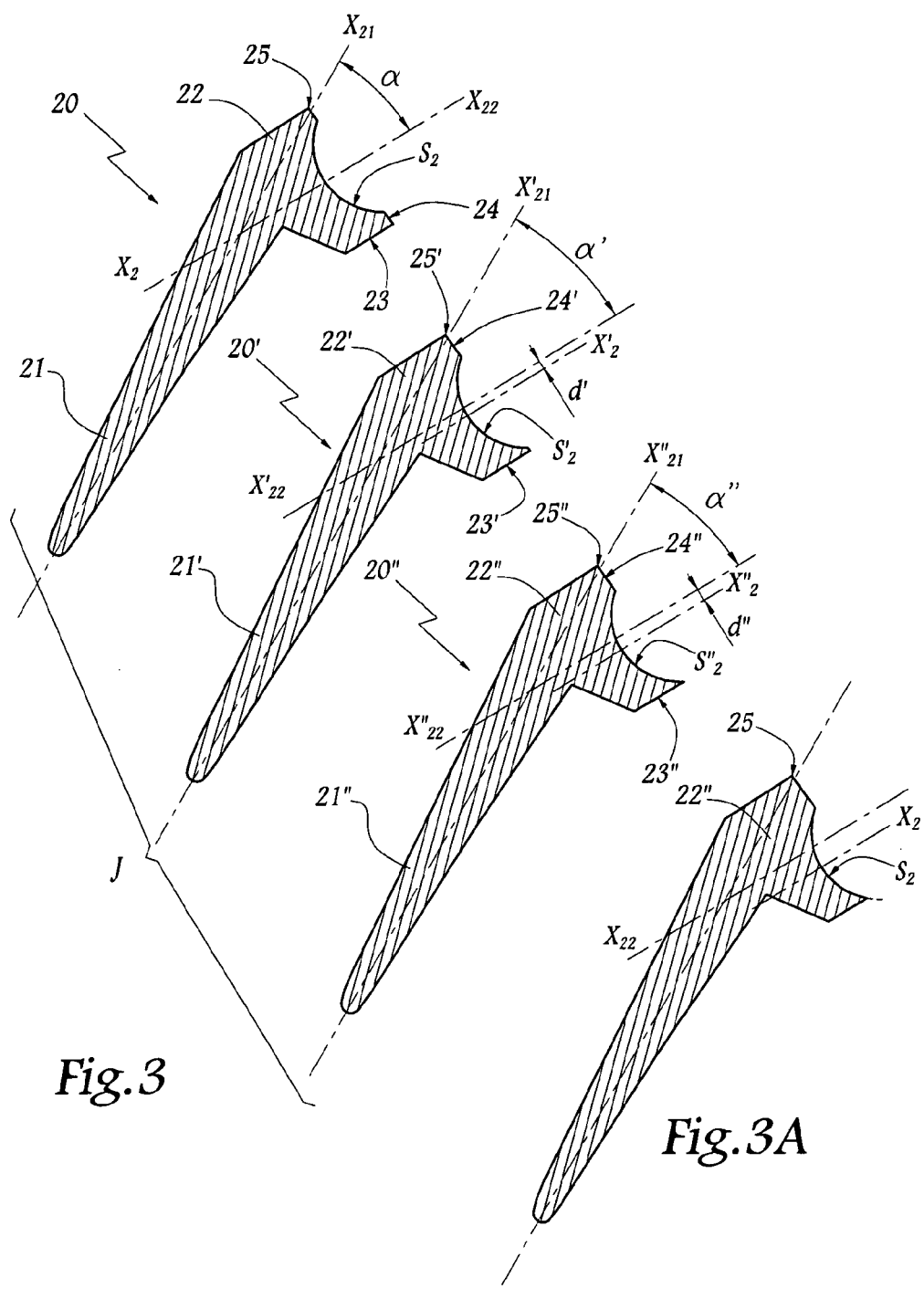
FIG. 3 schematically shows a set of humeral components according to the invention, shown in section.
FIG. 3A is a further humeral component that might belong to the set of components shown in FIG. 3.

According to the invention, and as is more particularly visible in FIG. 3, a set J of humeral components is provided, in which a plurality of components 20, 20' and 20" are prepared with different geometries.

As is visible in FIG. 3, the different components 20, 20' and 20" of the set J present globally the same outer shape, their respective stems 21, 21' and 21" having substantially the same outer shape, like their metaphyseal parts 22, 22' and 22". In particular, the outer radial surfaces 23, 23' and 23" of these different metaphyseal parts as well as their edges 25, 25' and 25" have substantially the same geometry.

$X_{21}$ $X'_{21}$ and $X''_{21}$ respectively denote the median axes of the anchoring stems 21, 21' and 21".

Furthermore, axis $X_2$ is defined by the axis of symmetry of the surface $S_2$.

For the component 20, axes $X_2$ and $X_{22}$ are merged.

As previously, axis $X'_{22}$ is defined as the central axis of the metaphyseal part 22' for the component 20' and axis $X'_2$ as the axis of symmetry of the concave surface of articulation $S'_2$ of the component 20'. Axes $X'_2$ and $X'_{22}$ are parallel to each other and offset by a non-zero distance d'. In the same way, axes $X''_{22}$ and $X''_2$ are defined as being respectively the central axis of the metaphyseal part 22" and the axis of symmetry of the surface $S''_2$, these axes being parallel and offset by a distance d" greater than distance d'.

An angle of inclination α between the axes $X_{21}$ and $X_{22}$, is also the angle of inclination between the axes $X_2$ and $X_{21}$ since axes $X_2$ and $X_{22}$ are parallel. The angle α' between axes $X'_{21}$ and $X'_{22}$ and the angle α" between axes $X''_{21}$ and $X''_{22}$ have the same value as angle α.

However, such equality of the angles α, α' and α" is not obligatory insofar as the axes $X_2$ and $X_{22}$, $X'_2$ and $X'_{22}$, $X''_2$ and $X''_{22}$ are not necessarily parallel.

The different components 20, 20' and 20" of the set J are therefore distinguished from one another by the fact that their concave surface of articulation $S_2$, $S'_2$, $S''_2$ is more or less offset with respect to the central axis of their end surface 24, 24' or 24". Except for the component 20, the axes $X'_2$ or equivalent of the concave articular surfaces are closer than the axes $X'_{22}$ and $X''_{22}$ to that part of the edge 25 most remote from axis $X'_{21}$ or equivalent. In other words, the surfaces $S'_2$ and $S''_2$ are offset downwardly in FIG. 3 with respect to the median position occupied by the surface $S_2$ vis-à-vis the surfaces 23 and 24 of the component 20.

The concave surface $S''_2$ of the component 20" extends to the immediate vicinity of the edge 25" at a point or area most remote from the stem 21", and thus the surface 24" is essentially of zero width in this area. The risks of interferences with the pillar of the scapula $G_1$ are therefore particularly limited in this case.

In this way, and as shown in FIG. 2, a prosthesis P" equipped with the component 20" has less chance of interfering with the pillar $G_1$ of the scapula, even if the latter has the same geometry as that shown in solid lines in FIG. 1.

When a shoulder prosthesis is installed, the surgeon cuts the bones and pre-positions the glenoid component or a phantom component. He may then select from the set J the most appropriate humeral component, possibly after testing with phantom components, in order to minimize the risks of interference. In a variant, the surgeon may pre-select the humeral component to be used, during the pre-op check-up.

The invention therefore enables the surgeon, by a reasoned selection of the humeral component 20, 20', 20" or equivalent from the set J of components, to adapt the relative position of the glenoid and humeral components when their respective surfaces of articulation cooperate, while avoiding or limiting to a very considerable degree the interferences between an edge 25 or equivalent of the humeral component and the pillar of the scapula. The invention also makes it possible to "verticalize" the humerus, or render it more vertical, at the end of adduction stroke.

In the set J, the humeral components have substantially the same outer geometry, except for the positioning of their concave articular surface. It is obvious that the different sets J may be provided in different sizes in order to adapt to the morphologies of the patients to be treated, or that a set J of humeral components may incorporate components of different heights. In addition, the number of components of the same set is not limited to three and may take any value greater than two, as a function of the precision desired for the adjustment of the offset d', d", etc. . . . .

According to a variant of the invention shown if FIG. 3A, the offset between the axes $X_2$ and $X_{22}$ may be even greater than that referenced d" in FIG. 3, in which case the surface $S_2$ is intersected by the edge 25. Such a variant makes it possible to offset the surface $S_2$ downwardly even more, it being understood that the center of rotation is located on the surface $S_2$.

Figure 4:
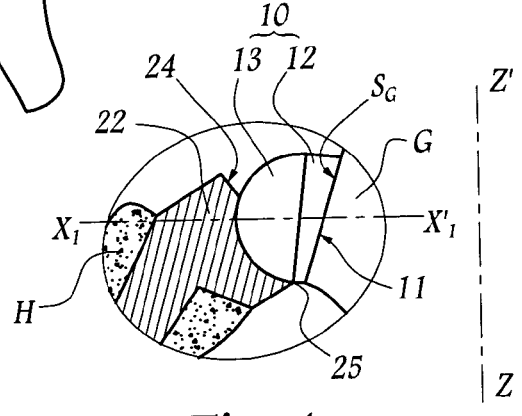
FIG. 4 is a view similar to FIG. 1A for a prosthesis of which the humeral component is identical to that of FIG. 2, the glenoid component being different.

As shown in FIG. 4, the milled surface $S_G$ of the glenoid cavity is not always parallel to a vertical axis Z-Z' passing through a center of the spinal column of the patient in standing position. Now, for a correct cooperation of the surfaces $S_1$ and $S_1$, it is preferable if the axis of symmetry $X_1$-$X'_1$ of the hemispherical surface $S_1$ is substantially perpendicular to axis Z-Z'. This is why, in the case of the surface $S_G$ being inclined as shown in FIG. 4, a glenoid component 10, of which the rear face 11 is not perpendicular to axis $X_1$-$X'_1$, is used, this making it possible to position the component 10 so that this axis $X_1$-$X'_1$ is substantially perpendicular to axis Z-Z'.

The component 10 may be formed by a base 12 and a cap 13, defining the surface $S_1$ and mounted on the base 12. The rear face 11 of the base 12 is in that case advantageously non-parallel to its front face on which the cap 13 is mounted.

A component 10 as shown in FIG. 4 may advantageously be selected from a set of components presenting variable differences in orientation between their respective rear faces and the axis of the surfaces $S_1$ that they define.

The invention has been shown with humeral components in one piece. In practice, and according to an aspect of the invention (not shown), the metaphyseal parts of these components are most often equipped with cups made of plastics material defining the surfaces $S_2$ of these components.

According to a variant of the invention (not shown), the axis of symmetry of the surface $S_1$ may be offset downwardly when the patient is in standing position, with respect to the axis of symmetry of the base on which the cap defining this surface is mounted.

This may be combined with the non-perpendicularity of the axis $X_1$–$X'_1$ and of the rear face of the prosthesis mentioned hereinabove with reference to the form of embodiment of FIG. 4.

What is claimed is:

1. A set of humeral components for a total shoulder prosthesis, each of the components comprising an anchoring stem and a metaphyseal part, the metaphyseal part including a concave surface of articulation in a form of a portion of a sphere formed in an end surface thereof, wherein an offset between an axis of symmetry of the concave surface and a central axis of the end surface of the metaphyseal part of the components is different for each component of the set, and wherein for each component, an orientation and position of the axis of symmetry of the concave surface is non-adjustably fixed with respect to the central axis of the end surface of the metaphyseal part thereof.

2. The set of components of claim 1, wherein, for each component, the axis of symmetry and the central axis are substantially parallel.

3. The set of components of claim 1, wherein, for at least one of the components, the axis of symmetry is located, with respect to the central axis, on an opposite side of a median axis of the stem.

4. The set of components of claim 3, wherein the end surface of the metaphyseal part of each of the components defines an outer edge, the surface of articulation of at least one of the components extends to an immediate vicinity of the edge of the metaphyseal part along a portion of the edge that is spaced opposite another portion of the edge that is generally in line with the median axis of the stem.

5. The set of components of claim 3, wherein the end surface of the metaphyseal part of each of the components defines an outer edge, the surface of articulation of at least one of the components is intersected by the edge of the metaphyseal part along a portion of the edge that is spaced opposite another portion of the edge that is generally in line with the median axis of the stem.

6. The set of components of claim 1, wherein the components have substantially the same shape with an exception of positions of the articular surfaces in the metaphyseal part.

7. The set of components of claim 1, wherein an angle of inclination of the axis of symmetry with respect to a median axis of the stem has substantially the same value for each of the components.

8. The set of components of claim 1, wherein for one of the components, the offset is zero, the axis of symmetry and the central axis being merged.

9. A total shoulder prosthesis comprising, a glenoid component and a humeral component, a set of humeral components comprising;
  each component of the set of humeral components being formed having an anchoring stem and a metaphyseal part, the metaphyseal part including a concave surface of articulation in a form of a portion of a sphere formed in an end surface thereof, wherein an offset between an axis of symmetry of the concave surface and a central axis of the end surface of the metaphyseal part of the components is different for each component of the set, wherein for each component, an orientation and position of the axis of symmetry of the concave surface is non-adjustably fixed with respect to the central axis of the end surface of the metaphyseal part thereof, and the humeral component being selected from the set of humeral components.

10. The total prosthesis of claim 9, wherein the glenoid component includes a convex surface of articulation that is centered on an axis of symmetry which is not perpendicular to a rear face of the glenoid component that is adapted to come into abutment against a glenoid cavity.

11. The set of components of claim 1 wherein the central axis is offset from the axis of symmetry of the concave surface so that the anchoring stem is adapted to be generally parallel to a sagittal plane at the end of adduction.

12. The set of components of claim 1 wherein the metaphyseal parts and the concave surfaces comprise separate components.

13. A set of humeral components for a total shoulder prosthesis, the humeral components comprising:
  a first humeral component comprising a first anchoring stem and a first metaphyseal part, an end surface of the first metaphyseal part includes an outer peripheral edge and a generally spherical concave surface of articulation, a distance between an edge of the generally spherical concave surface and the outer peripheral edge varies around at least a portion of a perimeter of the metaphyseal part; and
  a second humeral component comprising a second anchoring stem and a second metaphyseal part, an end surface of the second metaphyseal part includes an outer peripheral edge and a generally spherical concave surface of articulation, a distance between an edge of the generally spherical concave surface and the outer peripheral edge varies around at least a portion of a perimeter of the second metaphyseal part differently than the distance varies around the perimeter of the first metaphyseal part.

14. The set of humeral components of claim 13 wherein the distance between the edge of the generally spherical concave surface and the outer peripheral edge is substantially zero around at least a portion of a perimeter of at least the first metaphyseal part.

15. The set of humeral components of claim 13 wherein the distance between the edge of the generally spherical concave surface and the outer peripheral edge comprises a generally annular surface on at least the first metaphyseal part.

16. The set of humeral components of claim 13 wherein the end surface of the first metaphyseal part comprises a central axis and the generally spherical concave surface comprises an axis of symmetry that is collinear with the central axis.

17. The set of humeral components of claim 13 wherein the end surface of the first metaphyseal part comprises a central axis that is separated from an axis of symmetry of the generally spherical concave surface by a first offset.

18. The set of humeral components of claim 17 wherein the end surface of the second metaphyseal part comprises a central axis that is separated from an axis of symmetry of the generally spherical concave surface by a second offset, wherein the first offset is different than the second offset.

19. The set of humeral components of claim 13 wherein the end surface of the first metaphyseal part comprises a central axis offset from an axis of symmetry of the generally spherical concave surface so that the first anchoring stem is adapted to be generally parallel to a sagittal plane at the end of adduction.

20. The set of humeral components of claim 13 wherein the end surface of the first metaphyseal part comprises a central axis located on an opposite side of a median axis of the first anchoring stem with respect to an axis of symmetry of the generally spherical concave surface.

21. The set of humeral components of claim 13 wherein the end surface of the first metaphyseal part comprises a central axis that is non-adjustably fixed with respect to an axis of symmetry of the generally spherical concave surface.

22. The set of humeral components of claim 13 wherein the first metaphyseal part and the generally spherical concave surface comprise separate components.

23. The set of humeral components of claim 13 wherein an angle between a central axis of a metaphyseal part and a median axis of the stem is substantially the same for the first and second humeral components.

24. The set of humeral components of claim 13 wherein the first metaphyseal part comprises an outer radial surface parallel to a central axis, and the central axis is offset from an axis of symmetry of the generally spherical concave surface.

25. The set of humeral components of claim 13 wherein the outer peripheral edge on the first metaphyseal part is generally circular, the outer peripheral edge comprising a central axis that is offset from an axis of symmetry of the generally spherical concave surface.

26. The set of humeral components of claim 25 wherein the outer peripheral edge on the second metaphyseal part is generally circular, the outer peripheral edge on the second metaphyseal part comprising a central axis that is offset from an axis of symmetry of the generally spherical concave surface by an amount different than the offset on the first metaphyseal part.

27. The set of humeral components of claim 13 wherein the first and second metaphyseal parts comprises substantially the same shape except for the first and second spherical concave surfaces.

28. The set of humeral components of claim 13 comprising a third humeral component comprising a third anchoring stem and a third part, an end surface of the third metaphyseal part includes an outer peripheral edge and a generally spherical concave surface of articulation, a distance between an edge of the generally spherical concave surface and the outer peripheral edge is generally constant around at least a portion of a perimeter of the third metaphyseal part.

29. A set of humeral components for a total shoulder prosthesis, the humeral components comprising:
   a first humeral component comprising a first anchoring stem and a first metaphyseal part, an end surface of the first metaphyseal part includes an outer peripheral edge and a generally spherical concave surface of articulation, a distance between an edge of the generally spherical concave surface and the outer peripheral edge is generally constant around at least a portion of a perimeter of the first metaphyseal part; and
   a second humeral component comprising a second anchoring stem and a second metaphyseal part, an end surface of the second metaphyseal part includes an outer peripheral edge and a generally spherical concave surface of articulation, a distance between an edge of the generally spherical concave surface and the outer peripheral edge varies around at least a portion of a perimeter of the second metaphyseal part.

30. A set of humeral components for a total shoulder prosthesis, in which each component is formed having an anchoring stem and a metaphyseal part, the metaphyseal part including a concave surface of articulation in a form of a portion of a sphere formed in an end surface thereof, wherein an offset between an axis of symmetry of the concave surface and a central axis of the end surface of the metaphyseal part of the components is different for at least two components of the set, and wherein for each component an angle of inclination of the central axis with respect to a median axis of the anchoring stems has substantially the same value for each component.

31. A set of humeral components for a total shoulder prosthesis, the humeral components comprising:
   a first humeral component comprising a first anchoring stem and a first metaphyseal part with a central axis, an end surface of the first metaphyseal part includes a generally spherical concave surface of articulation with an axis of symmetry offset from the central axis; and
   a second humeral component comprising a second anchoring stem and a second metaphyseal part with a central axis, an end surface of the second metaphyseal part includes a generally spherical concave surface of articulation with an axis of symmetry offset from the central axis, wherein the first offset is different than the second offset.

32. The set of humeral components of claim 31 comprising a third humeral component comprising a third anchoring stem and a third metaphyseal part with a central axis, an end surface of the third metaphyseal part includes a generally spherical concave surface of articulation with an axis of symmetry offset from the central axis, wherein the third offset is different from the first and second offsets.

33. The set of humeral components of claim 31 wherein the central axis of at least the first metaphyseal part is non-adjustably fixed with respect to an axis of symmetry.

34. The set of humeral components of claim 31 wherein the first metaphyseal part and the generally spherical concave surface comprise separate components.

35. The set of humeral components of claim 31 wherein at least the first humeral component comprises one piece.

36. The set of humeral components of claim 31 wherein the distance between an edge of the generally spherical concave surface and an outer peripheral edge of the metaphyseal part is substantially zero around at least a portion of a perimeter of at least the first metaphyseal part.

37. The set of humeral components of claim 31 wherein the distance between an edge of the generally spherical concave surface and an outer peripheral edge of the first metaphyseal part comprises a generally annular surface.

38. The set of humeral components of claim 31 wherein the axis of symmetry is generally collinear with the central axis on the first metaphyseal part.

39. The set of humeral components of claim 31 wherein at least the first anchoring stem on the first humeral component is adapted to be generally parallel to a sagittal plane at the end of adduction.

40. The set of humeral components of claim 31 wherein an angle between the central axis and a median axis of the stem is substantially the same for the first and second humeral components.

41. The set of humeral components of claim 31 wherein an outer peripheral edge on at least the first metaphyseal part comprises a generally circular configuration.

42. A total shoulder prosthesis comprising:
the set of humeral components of claim 31; and
a glenoid component including a rear face adapted to come into abutment against a glenoid cavity and a convex surface of articulation centered on an axis of symmetry that is not perpendicular to the rear face.

43. A total shoulder prosthesis comprising:
the set of humeral components of claim 31; and
a glenoid component including a rear face adapted to come into abutment against a glenoid cavity and a convex surface of articulation centered on an axis of symmetry perpendicular to the rear face.

44. The set of humeral components of claim 13 wherein at least the first humeral component comprises one piece.

45. A total shoulder prosthesis comprising:
the set of humeral components of claim 13; and
a glenoid component including a rear face adapted to come into abutment against a glenoid cavity and a convex surface of articulation centered on an axis of symmetry that is not perpendicular to the rear face.

46. A total shoulder prosthesis comprising:
the set of humeral components of claim 13; and
a glenoid component including a rear face adapted to come into abutment against a glenoid cavity and a convex surface of articulation centered on an axis of symmetry perpendicular to the rear face.

47. The set of humeral components of claim 29 wherein the distance between the edge of the generally spherical concave surface and the outer peripheral edge is substantially zero around at least a portion of the perimeter of at least one of the metaphyseal parts.

48. The set of humeral components of claim 29 wherein the end surface of the second metaphyseal part comprises a central axis offset from an axis of symmetry of the generally spherical concave surface so that the second anchoring stem is adapted to be generally parallel to a sagittal plane at the end of adduction.

49. The set of humeral components of claim 29 wherein the end surface of at least one of the metaphyseal parts comprises a central axis that is non-adjustably fixed with respect to an axis of symmetry of the generally spherical concave surface.

50. The set of humeral components of claim 29 wherein at least one of the metaphyseal parts and the generally spherical concave surface comprise separate components.

51. The set of humeral components of claim 29 wherein at least the first humeral component comprises one piece.

52. The set of humeral components of claim 29 wherein an angle between a central axis of the metaphyseal parts and a median axis of the stem are substantially the same for the first and second humeral components.

53. The set of humeral components of claim 29 wherein the first and second metaphyseal parts comprise substantially the same shape except for the first and second spherical concave surfaces.

54. A total shoulder prosthesis comprising:
the set of humeral components of claim 29; and
a glenoid component including a rear face adapted to come into abutment against a glenoid cavity and a convex surface of articulation centered on an axis of symmetry that is not perpendicular to the rear face.

55. A total shoulder prosthesis comprising:
the set of humeral components of claim 29; and
a glenoid component including a rear face adapted to come into abutment against a glenoid cavity and a convex surface of articulation centered on an axis of symmetry perpendicular to the rear face.

* * * * *

UNITED STATES PATENT AND TRADEMARK OFFICE
CERTIFICATE OF CORRECTION

| | | |
|---|---|---|
| PATENT NO. | : 7,309,360 B2 | Page 1 of 1 |
| APPLICATION NO. | : 11/148377 | |
| DATED | : December 18, 2007 | |
| INVENTOR(S) | : Alain Tornier et al. | |

It is certified that error appears in the above-identified patent and that said Letters Patent is hereby corrected as shown below:

<u>Column 2, line 30</u>

Delete the word "a"

Signed and Sealed this

Twenty-ninth Day of April, 2008

JON W. DUDAS
*Director of the United States Patent and Trademark Office*